US00PP18329P2

(12) United States Plant Patent
Van Zanten

(10) Patent No.: US PP18,329 P2
(45) Date of Patent: Dec. 18, 2007

(54) *CHRYSANTHEMUM* PLANT NAMED 'GG GTCHA 05'

(50) Latin Name: *Chrysanthemum morifolium*
Varietal Denomination: GG GTCHA 05

(75) Inventor: Leo Van Zanten, Oxnard, CA (US)

(73) Assignee: GroLink Corporation, Oxnard, CA (US)

( * ) Notice: Subject to any disclaimer, the term of this patent is extended or adjusted under 35 U.S.C. 154(b) by 25 days.

(21) Appl. No.: 11/395,030

(22) Filed: Mar. 31, 2006

(51) Int. Cl.
*A01H 5/00* (2006.01)

(52) U.S. Cl. ..... Plt./295

(58) Field of Classification Search ..... Plt./295
See application file for complete search history.

(56) References Cited

PUBLICATIONS

Brummit, R.K.; "The Garden"; "*Chrysanthemum* once again," Sep. 1997; pp. 662–663. (2 pages total).*

* cited by examiner

*Primary Examiner*—Kent Bell
*Assistant Examiner*—S. B. McCormick-Ewoldt

(57) ABSTRACT

A new and distinct *Chrysanthemum* plant cultivar is disclosed, characterized by medium-size daisy type inflorescences, consistent flowering response to short days, blooming consistently after 52 days of short day length, bronze yellow ray florets with dark red underpetal, and a moderate branching habit.

1 Drawing Sheet

Latin name of the genus and species: *Chrysanthemum morifolium.*
Variety denomination: 'GG GTCHA 05'.

BACKGROUND OF THE INVENTION

The new cultivar 'GG GTCHA 05' was originated from a cross made by Leo Van Zanten in a planned breeding program in January 2001 between the male parent 'Miramar' (U.S. Plant Pat. No. 7,469) and the female parent 'Lucky Time' (U.S. Plant Pat. No. 10,777). The new cultivar was discovered and selected by Leo Van Zanten in August 2001 in Oxnard, Calif.

Asexual reproduction of the new cultivar 'GG GTCHA 05' by vegetative cuttings in Oxnard, Calif., and has shown that the unique features of this new cultivar are stable and reproduced true to type on successive generations.

SUMMARY OF THE INVENTION

The cultivar 'GG GTCHA 05' has not been observed under all possible environmental conditions. The phenotype may vary somewhat with variations in environment such as temperature, daylength, and light intensity, without, however, any variance in genotype.

The following traits have been repeatedly observed and are determined to be the unique characteristics of 'GG GTCHA 05.' These characteristics in combination distinguish 'GG GTCHA 05' as a new and distinct *Chrysanthemum* cultivar:

1. Medium-size daisy type inflorescence;
2. Yellow-bronze ray florets with dark red underpetal;
3. Moderate branching habit; and
4. Blooming consistently after 52 days of short day length.

Plants of the new cultivar 'GG GTCHA 05' are similar to plants of the male parent variety, 'Miramar' in most horticultural characteristics, however plants of the new cultivar 'GG GTCHA 05' are taller than the male parent. Also, the shape of the ray florets of the new cultivar are oblanceolate compared to the spoon-shape florets of 'Miramar.' Further, 'GG GTCHA 05' have smaller inflorescences and more orange-yellow ray florets than the male parent.

Plants of the new cultivar 'GG GTCHA 05' are similar to plants of the female parent variety, 'Lucky Time' in most horticultural characteristics, however plants of the new cultivar 'GG GTCHA 05' are taller than the female parent. Also, the male parent has anemone-type flowers compared to the daisy form of the new cultivar 'GG GTCHA 05'. Further, the new cultivar has yellow ray florets compared to the light pink ray florets of the female parent.

In comparison to the commercially available variety 'Bronze Cherie' (U.S. Plant Pat. No. 9,702), 'GG GTCHA 05' are taller than that of the comparable variety. Additionally, the new variety 'GG GTCHA 05' has larger inflorescence diameter. Further, the new variety 'GG GTCHA 05' has more yellow ray florets compared to the yellow-orange ray florets of 'Bronze Cherie'. Finally, 'GG GTCHA 05' has more green foliage than the yellow-green foliage of the comparable variety.

BRIEF DESCRIPTION OF THE PHOTOGRAPH

The accompanying photograph in FIG. 1 illustrates in full color a typical plant of 'GG GTCHA 05' grown in a 6.5-inch container. Five cuttings were used in the pot, planted late October and grown in a greenhouse. The colors are as nearly true as is reasonably possible in a color representation of this type.

DETAILED BOTANICAL DESCRIPTION

In the following description, color references are made to The Royal Horticultural Society Colour Chart except where general terms of ordinary dictionary significance are used.

The following observations and measurements describe 'GG GTCHA 05' plants grown in Oxnard, Ventura County, Calif., during the winter months. The growing temperature in the greenhouse ranged from 67° F. and 78° F. Measurements and numerical values represent averages of typical flowering types.

Botanical classification: *Chrysanthemum morifolium* cultivar 'GG GTCHA 05.'
Commercial classification: Pot-type *Chrysanthemum.*

PROPAGATION

Time to rooting: 7 to 14 days at approximately 21° C.
Root description: Fine, fibrous.

PLANT

Growth habit: Mounding herbaceous perennial.
Height: Approximately 34 cm.
Plant spread: Approximately 45 cm.
Growth rate: Moderate.
Branching characteristics: Moderate Branching.
Length of lateral branches: Approximately 32 cm.
Number of leaves per lateral branch: Approximately 35.
Age of plant described: Approximately 105 days.

FOLIAGE

Leaf:
*Arrangement.*—Alternate single.
*Average length.*—Approximately 6.2 cm.
*Average width.*—Approximately 3.6 cm.
*Shape of blade.*—Ovate.
*Apex.*—Acuminate.
*Base.*—Attenuate.
*Attachment.*—Stalked.
*Margin.*—Pinnately lobed, sinuses between lateral lobes parallel to divergent.
*Texture of top surface.*—Lightly pubescent.
*Texture of bottom surface.*—Lightly pubescent.
*Leaf internode length.*—Approximately 1.7 cm.
*Color.*—Young foliage upper side: Near Green 139A. Young foliage under side: Near Green 137B. Mature foliage upper side: Near Green 137A. Mature foliage under side: Near Green 137C.
*Venation.*—Type: Palmately net. Venation color upper side: Near Green 138C. Venation color under side: Near Green 138C.
Petiole:
*Average length.*—Approximately 1.6 cm.
*Color.*—Near Green 138B.
*Diameter.*—Approximately 0.3 cm.

BLOOM

Inflorescence:
*Flowering habit.*—Induced by darkness period greater than 13.5 hours, approximately 52 days of appropriate day length required to induce and develop blooms.
*Inflorescence form.*—Daisy.
*Number of inflorescences per lateral branch.*—Approximately 22.
*Inflorescence diameter.*—Approximately 5.6 cm.
*Inflorescence depth.*—Approximately 2 cm.
*Inflorescence longevity on plant.*—Approximately 35 to 42 days.
*Persistence.*—Persistent.
*Fragrance.*—None detected.
Ray florets:
*Appearance.*—Matte.
*Texture.*—Smooth.
*Average number of ray florets per inflorescence.*—30.
*Number of whorls.*—Approximately 2.
*Shape.*—Oblanceolate reflexed.
*Aspect.*—Semi-upright.
*Margin.*—Entire.
*Apex.*—Obtuse.
*Base.*—Fused along 20% of length.
*Length.*—Approximately 2.2 cm.
*Width.*—Approximately 0.6 cm.
*Color.*—Upper surface at first opening: Near Yellow-Orange 14A. Upper surface at maturity: Near Yellow 12A. Upper surface at fading: Near Yellow 13C. Under surface at first opening: Near Greyed-Purple 185A. Under surface at maturity: Near Greyed-Purple 185A with small streaks of near Yellow 12A. Under surface at fading: Near Greyed-Purple 184A with small streaks of near Yellow 13C.
Disc florets:
*Appearance.*—Matte.
*Texture.*—Smooth.
*Average number of florets per disc.*—Approximately 243.
*Shape.*—Cylindric.
*Apex.*—Obtuse.
*Average length.*—Approximately 0.2 cm.
*Average width.*—Approximately 0.1 cm.
*Color.*—At first opening: Near Yellow-Green 144B. At maturity: Near Yellow-Green 144C. At fading: Near Yellow 13B with near Yellow-Green 154B spots in center.
Peduncle:
*Length.*—At terminal end (shortest): Approximately 4 cm. At lateral end (longest): Approximately 6 cm.
*Angle to stem.*—Acute.
*Strength.*—Moderate.
*Color.*—Near Green 137C.
*Habit.*—Upright.
*Diameter.*—Approximately 0.2 cm.
*Surface texture.*—Lightly pubescent.
Inflorescence bud:
*Length.*—Approximately 0.6 cm.
*Diameter.*—Approximately 0.9 cm.
*Form.*—Globular.
*Color.*—Near Yellow-Green 145C.
Involucral bracts (phyllaries):
*Appearance.*—Matte.
*Texture.*—Lightly pubescent.
*Number.*—Approximately 25.
*Shape.*—Ovate.
*Margin.*—Entire.
*Apex.*—Acute.
*Length.*—Approximately 0.7 cm.
*Width.*—Approximately 0.3 cm.
*Color.*—Upper side: Near Green 137A. Under side: Near Green 137A.

REPRODUCTIVE ORGANS

Ray florets:
*Number of pistils per floret.*—1.
*Stigma shape.*—2 branched.
*Stigma color.*—Near Yellow 12A.

*Style color.*—Near Yellow-Green 149C.

*Style length.*—Approximately 0.4 cm.

*Stamens.*—Absent.

Disc florets:

*Number of pistils per floret.*—1.

*Stigma shape.*—Cylindric.

*Stigma color.*—New Yellow 12A.

*Style length.*—Approximately 0.3 cm.

*Style color.*—Near Yellow-Green 145C.

*Number of stamens per floret.*—Approximately 5.

*Anther shape.*—Tubular.

*Anther color.*—Near Yellow-Orange 14A.

*Pollen color.*—Near Yellow-Orange 14A.

OTHER CHARACTERISTICS

Disease resistance: Neither resistance nor susceptibility to diseases or pests has been observed in this variety.

Drought tolerance/cold tolerance: Flowering plants are hardy to low temperatures about −2° C. Non-flowering plants are hardy in the approximately range of 3° C. to −6° C., depending upon duration of cold and amount of moisture in the soil. With adequate water plants are hardy to a high temperature of 45° C.

Fruit/seed production: Commercially, this plant is not used or observed in a stage where seeds would be produced. Therefore, seed production has not been observed.

What is claimed is:

1. A new and distinct cultivar of *Chrysanthemum* plant named 'GG GTCHA 05' as herein illustrated and described.

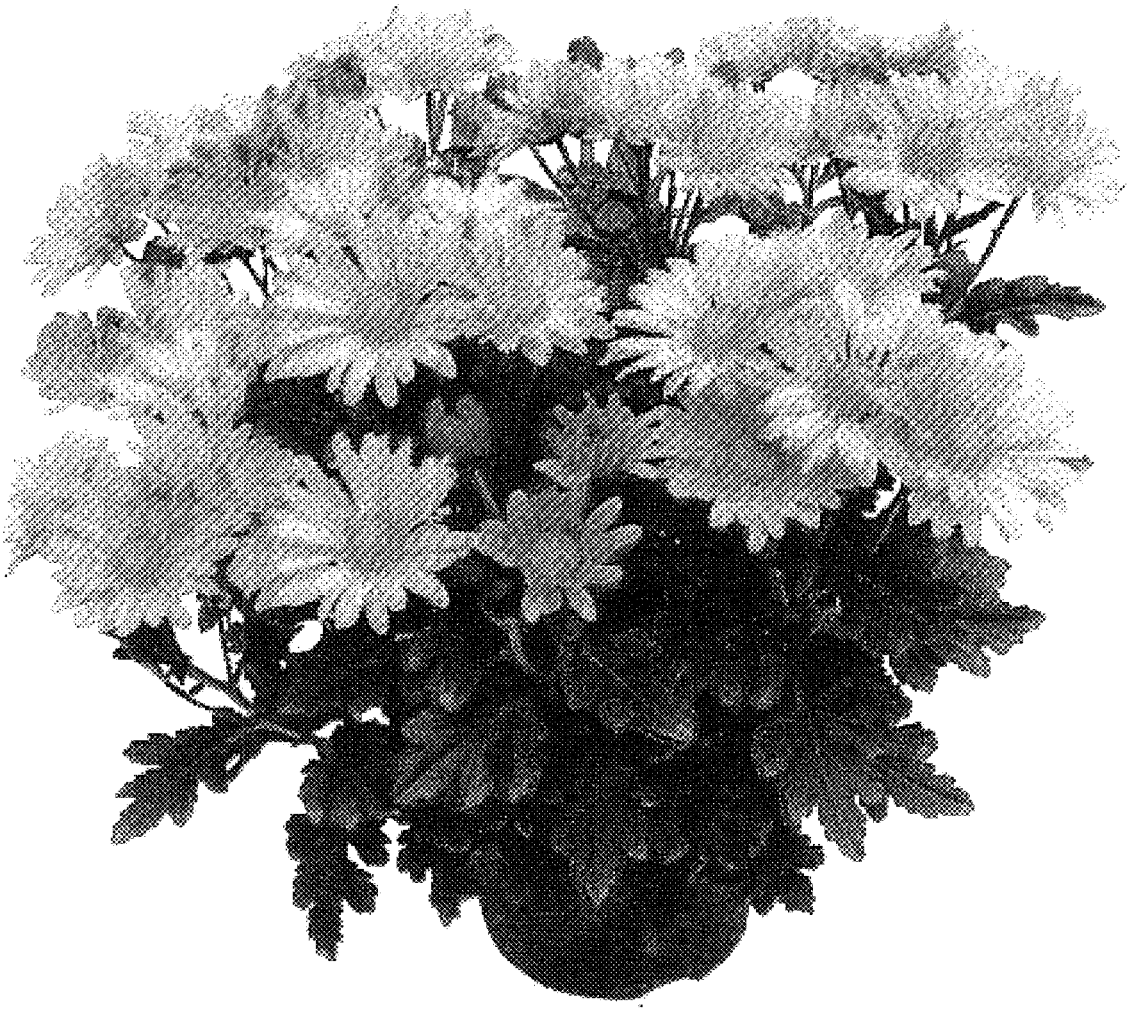

* * * * *